(12) United States Patent
Carlson et al.

(10) Patent No.: US 8,097,766 B2
(45) Date of Patent: Jan. 17, 2012

(54) SELF-ADHERING FRICTION REDUCING LINER AND METHOD OF USE

(75) Inventors: J. Martin Carlson, Mora, MN (US); Stacey R. Stoll, Minneapolis, MN (US)

(73) Assignee: Tamarack Habilitation Tehnologies, Inc., Blaine, MN (US)

( * ) Notice: Subject to any disclaimer, the term of this patent is extended or adjusted under 35 U.S.C. 154(b) by 548 days.

(21) Appl. No.: 11/590,638

(22) Filed: Oct. 31, 2006

(65) Prior Publication Data

US 2007/0043316 A1 Feb. 22, 2007

Related U.S. Application Data

(60) Continuation of application No. 10/027,949, filed on Dec. 21, 2001, now abandoned, which is a division of application No. 09/094,888, filed on Jun. 15, 1998, now Pat. No. 6,362,387.

(51) Int. Cl.
*A61F 13/00* (2006.01)
(52) U.S. Cl. ............... 602/41; 602/42; 602/54; 602/57
(58) Field of Classification Search ............ 602/41, 602/42, 52, 54, 57
See application file for complete search history.

(56) References Cited

U.S. PATENT DOCUMENTS

| | | | |
|---|---|---|---|
| 526,057 A | 9/1894 | Rowley | |
| 812,275 A | 2/1906 | Kespohl | |
| 1,099,938 A | 6/1914 | Rowley | |
| 2,634,424 A | 4/1953 | O'Gorman | 3/20 |
| 2,898,910 A | 8/1959 | Gross et al. | 602/59 |
| 2,943,623 A * | 7/1960 | Thompson | 128/893 |
| 3,393,407 A | 7/1968 | Kandel | 3/20 |
| 3,548,420 A | 12/1970 | Spence | 3/20 |
| 3,732,578 A | 5/1973 | Pollack | 3/19 |
| 4,128,903 A | 12/1978 | Marsh et al. | 3/19 |
| 4,959,059 A | 9/1990 | Eilender et al. | 604/358 |
| 5,019,064 A | 5/1991 | Eilender | 604/378 |
| 5,154,682 A | 10/1992 | Kellerman | 36/44 |
| 5,188,124 A * | 2/1993 | Feret | 128/889 |
| 5,397,628 A | 3/1995 | Crawley et al. | 428/246 |
| 5,464,443 A | 11/1995 | Wilson et al. | 623/37 |
| 5,590,420 A | 1/1997 | Gunn | 2/69 |
| 5,899,207 A | 5/1999 | Scheinberg | 128/882 |
| 6,067,987 A | 5/2000 | Scheinberg | 128/882 |

* cited by examiner

*Primary Examiner* — Kim M Lewis

(74) *Attorney, Agent, or Firm* — Westman, Champlin & Kelly, P.A.; Z. Peter Sawicki

(57) ABSTRACT

A patch of low friction materials, such as a film of polytetrafluoroethylene is sized to provide an area of low friction support for a portion of a human body relative to an object such as a shoe or prosthetic socket. The patch can be lined with foam, or preferably, a stretch fabric so that it will fit around irregular contours of the shoe, or socket, or the skin itself. The patches reduce shear trauma in critical load areas. After identifying regions of high loads, the method comprises applying the patches as needed to avoid sores, calluses, blisters and abrasions.

1 Claim, 8 Drawing Sheets

SELF-ADHERING FRICTION REDUCING LINER AND METHOD OF USE

CROSS REFERENCE TO RELATED APPLICATIONS

This application is a continuation of U.S. Application Ser. No. 10/027,949, filed on Dec. 21, 2001, which is a divisional of U.S. Ser. No. 09/094,888, filed Jun. 15, 1998, now U.S. Pat. No. 6,362,387, issued on. Mar. 26, 2002, the content of which is hereby incorporated by reference in their entireties.

BACKGROUND OF THE INVENTION

The present invention relates to the use of very low friction material formed into patches or pieces and adhered to the skin or to a surface in contact with the skin (or immediately adjacent material such as a sock) to lower the magnitude of tangential traction of the surface in contact with the skin. The material reduces the likelihood of abrasion, trauma and ulceration in localized areas.

In the prior art, there have been efforts to reduce the co-efficient of friction of materials in load bearing contact with the skin, such as the surface of a lining of a shoe, which slides against a stocking. Also the regions where a limb prosthesis is in load bearing contact with a residual limb have been extensively considered for ways of reducing problems. The co-efficient of friction of smooth leather varies, depending on the moisture content, and when it gets wet can be quite high in friction. Moleskin patches have been sold and used for covering corns on the feet, as well as covering calluses, but this also has a relatively high co-efficient of friction against the inner surface of a shoe and the co-efficient of friction increases substantially when the moleskin is wet.

Blisters, abrasions, calluses, bursas and even some forms of sub-cutaneous tissue trauma are the result of applications of a combination of forceful contact and tangential tractions to the skin (forceful rubbing/forceful shearing). High shear stresses may cause damage in a single cycle. Low shear stresses may cause tissue damage when the number of cycles is great.

Tangential skin tractions relate directly to tissue shear stress and shear strain magnitudes. Shear strain is by its very nature very distortional and, when it exceeds certain levels, results in the tearing of biological tissues such as blood capillaries and interface (skin-subcutaneous) layers. High normal pressures (perpendicular to the skin surface) in the absence of significant tangential tractions are surprisingly well tolerated by skin and underlying tissue, especially when applications are of a short enough duration to avoid ischemic trauma (cell death after an extended period of blood flow blockage).

This invention is primarily aimed at reducing and preventing shear trauma from many repetitions of short duration skin loadings, but eliminating shear tractions even in low repetition, long-duration loadings is of value. Research shows that even capillary blood flow is affected strongly by whether or not shear stresses are superimposed on normal pressures. When high shear stresses are present, capillary blood flow has been shown to be occluded at normal pressures only half as great as what are required to occlude flow in the absence of shear stresses and strains.

There is some recognition among medical researchers and care-givers that shear plays a role in tissue trauma. However, how and when excessive shear stresses/strains occur and how they damage tissue are hard to visualize. Injury from a normal force (a simple, yet forceful, blow or bump causing injury by crushing tissue) is easier for people to visualize and understand. Shear stresses and how they vary over a given area (and vary with time) are very hard to measure; much harder than it is to measure normal pressure. In addition to the visualization and measurement difficulties just mentioned, there is the fact that few people have better than a vague qualitative awareness of how something called the "coefficient of friction" (C.F.) relates to blisters, abrasions, and calluses. Tangential traction force magnitudes can be no greater than the C.F. times the magnitude of normal force. Therefore, the simplest, most direct way to reduce shear induced tissue trauma is to choose materials which minimize friction against the at-risk skin surface areas. Until the present invention, there has been little practical awareness of, and attention given to, friction management.

Examination and knowledge of products on the market indicate that the opportunities for reducing callusing, blistering and abrasions by friction management has been almost entirely unappreciated by designers of shoes, orthoses, prostheses, and many other objects that come in repeated or prolonged contact with the human body.

Thin silk or synthetic fiber sheets have been used by amputees to pull over their residual limbs before pulling on a cotton or wool sock and then donning the limb prosthesis. The co-efficient of friction between the sheet and the sock is reduced under dry conditions and does protect the residual limb to some extent from friction and consequent shear-related trauma. The coefficient of friction increases substantially when the material becomes damp or wet. In most cases, the material used to line shoes and prosthesis sockets, for example, represent high friction choices. Foam products are used to line prosthetic sockets, orthoses, and shoe insoles and represent a particularly poor material from the standpoint of friction management. Damp skin and sock material literally sticks to such foams.

Synthetic gel socket liners are available, and these are generally in the range of ⅛ to 5/16 inch thick. The liner cover tends to stick to the skin and other materials in contact with it, so that it does not act as a friction reducer, but does provide cushioning and accommodates small amplitude shear motions without much resistance. The effectiveness of a gel liner is dependent on its thickness, and as it becomes thicker, its weight and bulk are deterrents.

Thus, the concept of providing a very low friction interface between the skin and surfaces that contact the skin, particularly in high load and high shear areas, has escaped the workers in the field and the need exists for reduction of trauma to the skin where the skin and tissue are supported.

SUMMARY OF THE INVENTION

The present invention relates to providing a layer of material that has a very low friction outer surface in both dry and wet conditions to provide an interface with a surface that normally would support the skin either directly or through a cloth covering, such as a sock fabric. In the usual situation, the surface loading or bearing on the skin may be the inner surface of an orthosis, the socket surface of a prosthesis, or inner surfaces of a shoe, especially insoles, but also other inner surfaces. The layer of low-friction material is adhered, preferably, to the surface of the object that bears on the skin and faces the skin, although applying the layer with an adhesive directly on the skin in the affected area with the low friction surface facing the support is also contemplated. The purpose of the low friction material is to lower the magnitude of tangential tractions that the surface of the object can exert against the skin.

The use of intervening layers is contemplated in the present invention, so a sock or sheet placed between the low friction pad and the skin does not adversely affect the performance.

A low friction surface layer used may be on material in the form of a sheet, or a small patch that is pre-cut, or custom cut to a desired size, and having a pressure sensitive adhesive on the surface of the patch opposite from the low friction surface. The adhesive may be on the outer surface of another layer of material, such as a foam backing cushion layer or a stretch fabric backing bonded to the low friction material. A release paper is placed on the exposed adhesive. When the release paper is removed, the patch or piece of material providing the low friction surface layer can be adhered into a certain desired position of the surface of the skin or on the object that bears on the skin.

Preferably, the low friction layer is a thin film material having the surface friction characteristics of polytetrafluoroethylene (PTFE) The PTFE layer is preferably bonded to a fabric layer of a somewhat elastic, flexible material such as Lycra or a Lycra blend. The exposed side of the fabric is covered with a pressure adhesive and a release paper is on top of the adhesive.

The thin sheet of PTFE material can be used without any backing sheets by applying adhesive directly to the PTFE layer. Bonding a very thin sheet of PTFE to a stretch fabric without having the PTFE separate from the fabric during use gives the desired low friction characteristics of the outer surface, while permitting the formed patch to conform to irregular shapes or surfaces, because of the stretch fabric underneath the thin layer of PTFE. The stretch fabric also gives the thin layer of low friction material, such as PTFE, "body" so it can be handled reasonably during the release paper stripping and application of the layer or patch to the desired surface. Very thin layers of PTFE tend to wrinkle or fold and cause problems with getting them very smooth. The elasticity of the backing fabric allows conformance into recesses, over convexities, and onto a combination of compound contoured surfaces.

Cushioning material, such as foam can be placed between the patch and the surface supporting the patch, if desired, to provide a cushioning effect, as is known. Various shapes can be made, including shapes which would have the stretch fabric toward the center of the patch or piece so that it was surrounded by an adhesive coated thin low friction material.

A preferred method of use includes placement of suitable size pieces or patches of the low friction coefficient material either on the skin or on the surface that will be next to the skin in locations where shear trauma is likely to occur. These patches or pieces can be held in place with suitable adhesive on the back side of the low friction material. Foam or other compressible material for cushioning can be used wherever needed.

Another aspect or form of the protective patch is the PTFE film or layer bonded to a calf skin leather hide, textile foam liner, or other material that could be used to line the inner wall of the toe box of a shoe. The composite material can be sewn and applied in the same manner as the lining material now is applied without a PTFE film surface. The usefulness of this material is realized in its ability to shield dorsal and peripheral surfaces of the foot from damaging shear forces. At these non-plantar locations, high tangential tractions can be present, but more often trauma develops from lower forces, that generate excessive callus/corn growth and/or tissue breakdown by the action of cyclic (high frequency) loading.

The patches of the present invention offers an easy way to accomplish "friction management". The surfaces that a shoe, orthosis, or prosthesis present to the skin vary as to their function and as to the tissue trauma risk they present. It is also true that some areas of the anatomy within a shoe, prosthesis, or orthoses are at greater or lesser risk because of the level of peak forces and/or the amount of soft tissue interposed between skin and bone. Some parts of an orthosis bear only slightly or not at all against the corresponding skin surface. Other parts bear very firmly in order to provide maximum orthopedic support, correction, or weight bearing. Still other surfaces such as the supra-condylar parts of a BK (lower leg) prosthesis socket serve to suspend (during swing-through) or maintain position of the device.

All of these just-noted facts are important because they are reasons to vary the friction coefficient depending on the surface function. For instance, there is very little reason to be concerned about the friction coefficient of a surface in only very light contact with the skin (unless the number of repetitions is very high). Forceful cyclical contact against a skin surface is a situation that benefits more from minimizing the friction coefficient. If the area is "bony" minimizing friction becomes more important.

In a case like the supra-condylar suspension areas of the BK socket mentioned earlier, high friction (even "sticky") materials may be desired. Applying the low friction patches of an aspect of the invention to certain areas and not others is a way to add friction management to the orthotist's (prosthetist's, podiatrist's, etc.) treatment methods and appliances. In cases where the professional wishes to apply maximum supportive/corrective pressure the near elimination of friction and shear in selected regions means that much greater support can be safely provided without approaching tissue trauma conditions.

There are also many consumer (non-professional) applications for the present invention. Many people are plagued by excessive callus build-up. A person with excessive calluses under the metatarsal heads might remove the shoe insoles and apply low friction patches to the corresponding surface of the insole. If the excessive callus is in the form of "corns", the person could apply a low friction corn pad to relieve some pressure on a painful corn (by means of annular cushioning material) and greatly reduce the friction and shear which originally generated, and then maintains the corn callus.

A similar but much larger patch might be applied by a skater over ankle bones to allow tight(er) lacing with greater comfort and less chance of trauma at the apices of those bony prominences. As an alternative, the skater may choose to adhere the patch to the appropriate locations on the inside surface of the skate uppers. There are a myriad of other possibilities such as on kneeling pads (for cement workers, etc.) or on backpack shoulder straps.

A similar (but non-consumer) use of the cushioned patch (continuous, annular, or donut types) is in hospitals for prevention of bed sores. Low friction cushion patches of the present invention applied over healthy bony areas such as sacrum-coccyx, greater trochanter, heels, and elbows as a prophylactic measure act to inhibit the generation of bed sores.

Figure 5:
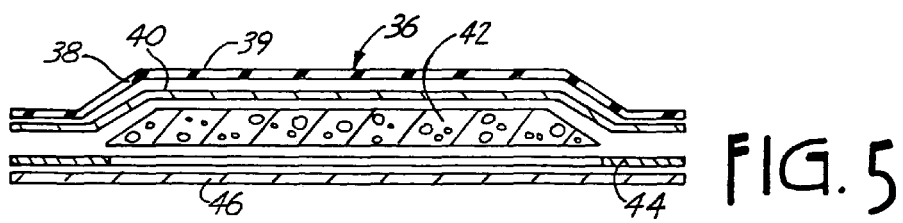
Figure 6:
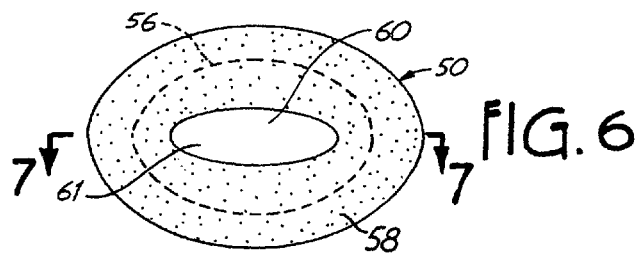
Figure 7:
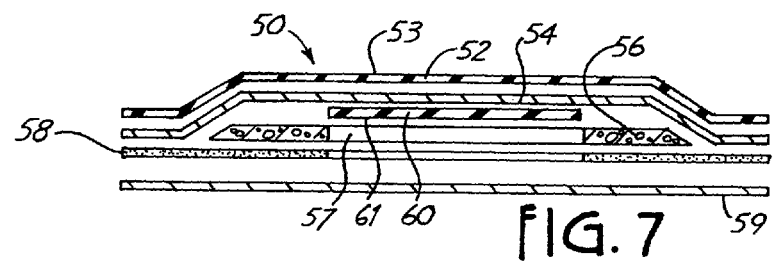
Figure 8:
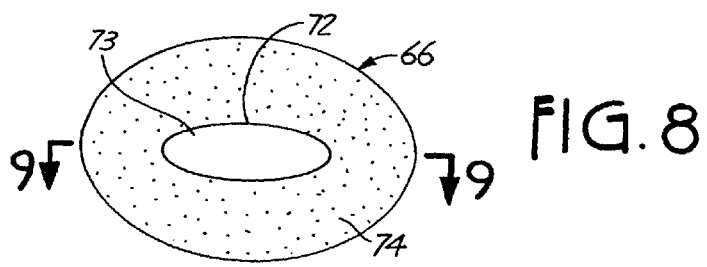
Figure 9:
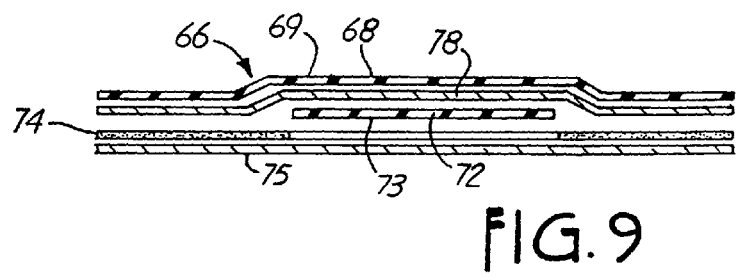
Figure 10:
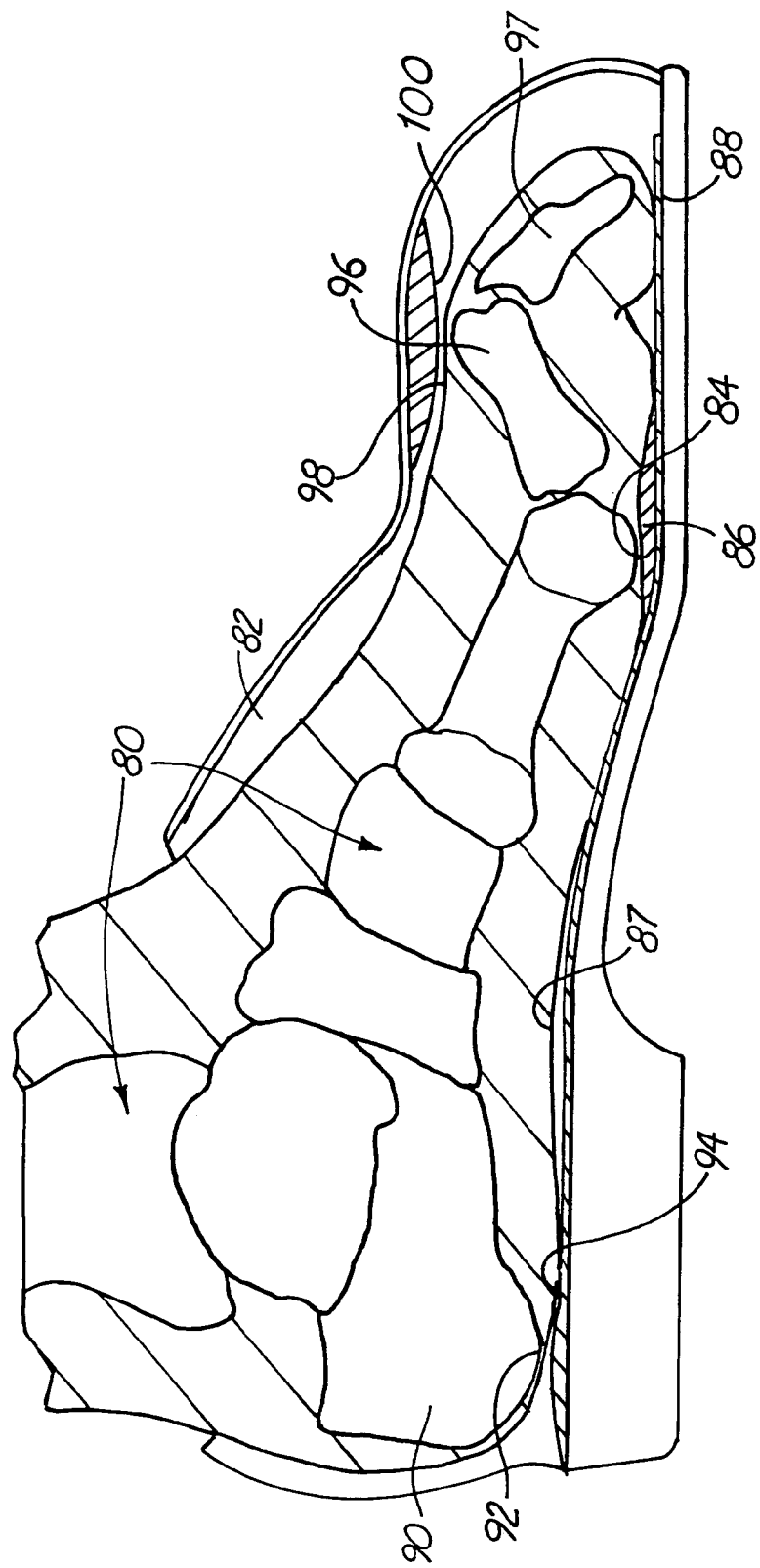
Figure 11:
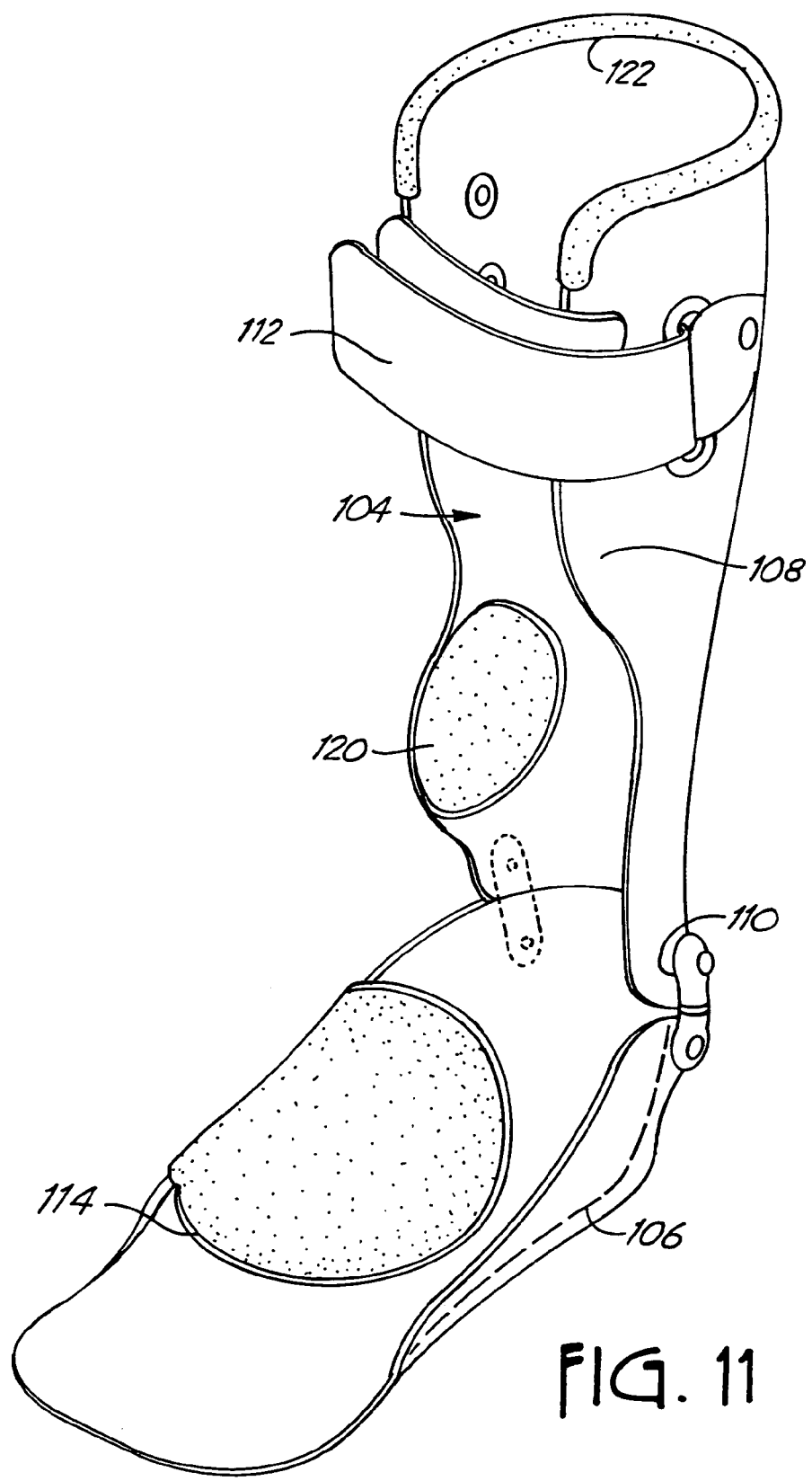
Figure 12:
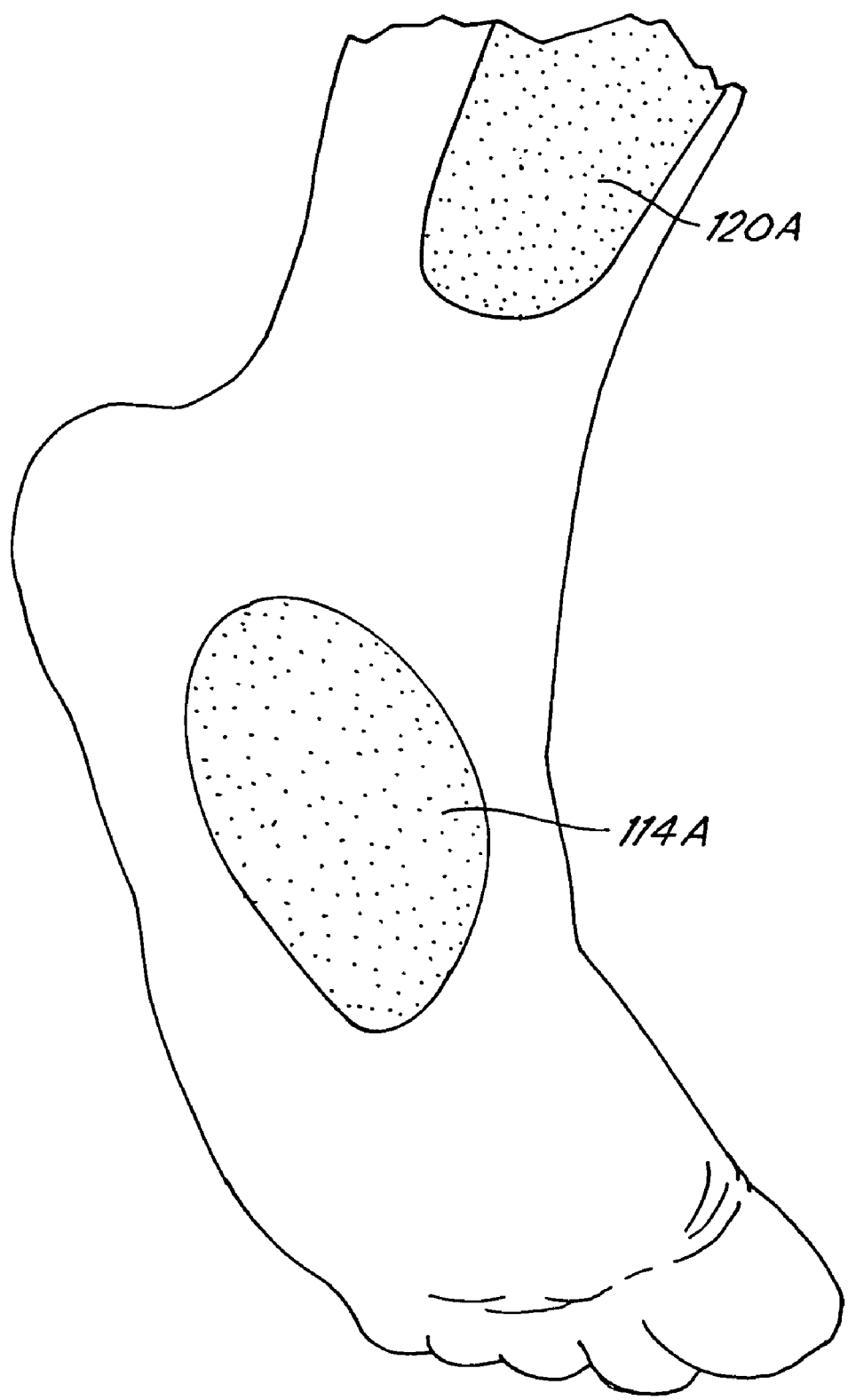
Figure 13:
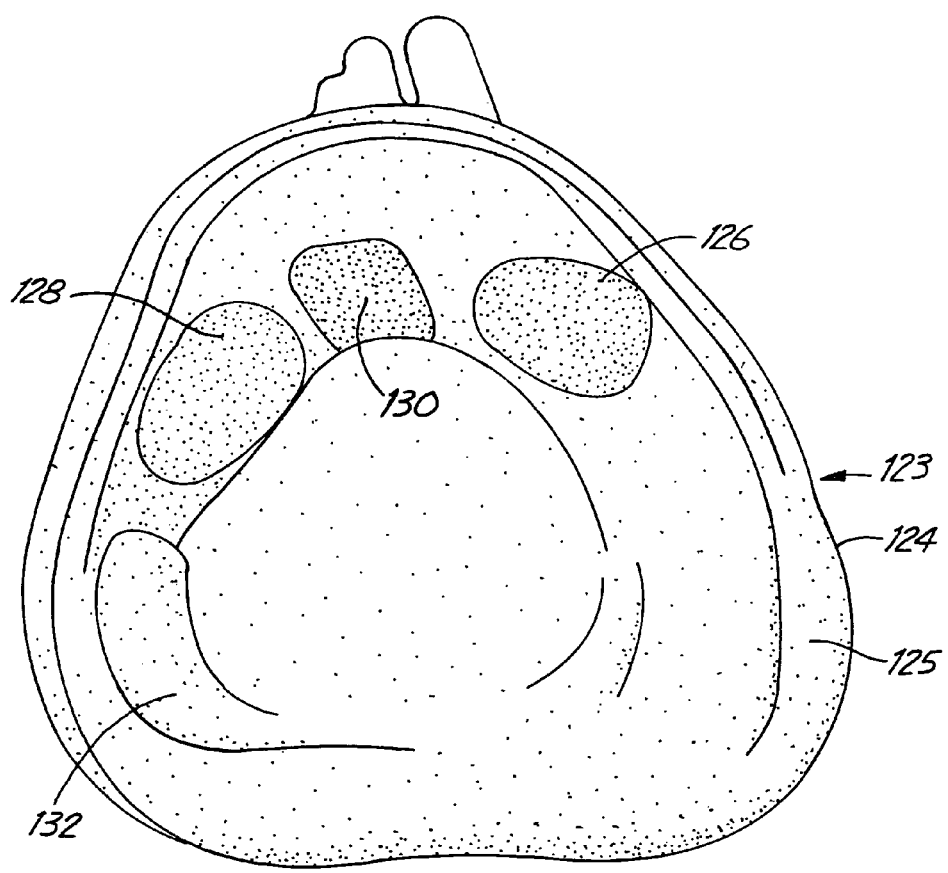
Figure 14:
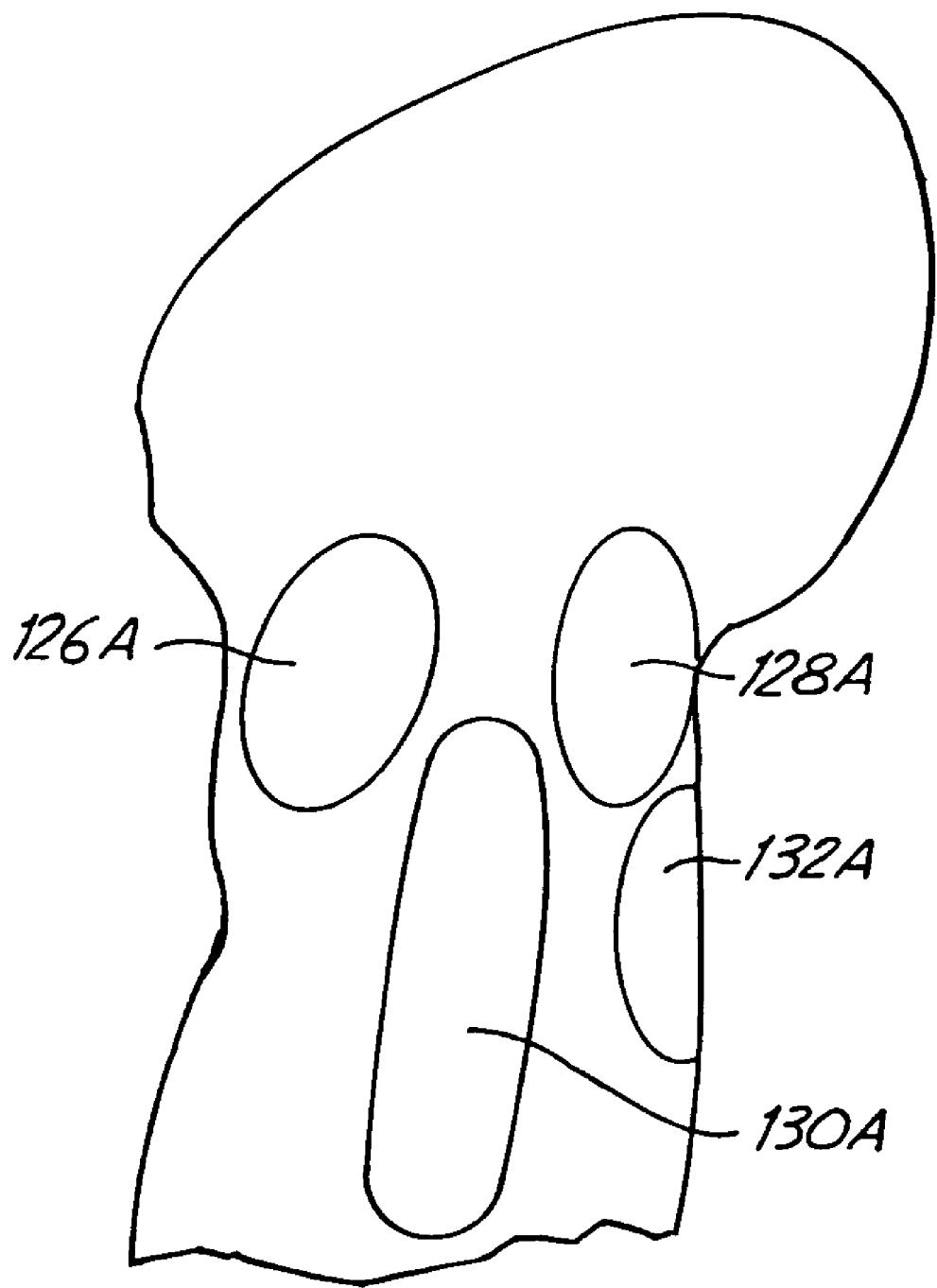
Figure 15:
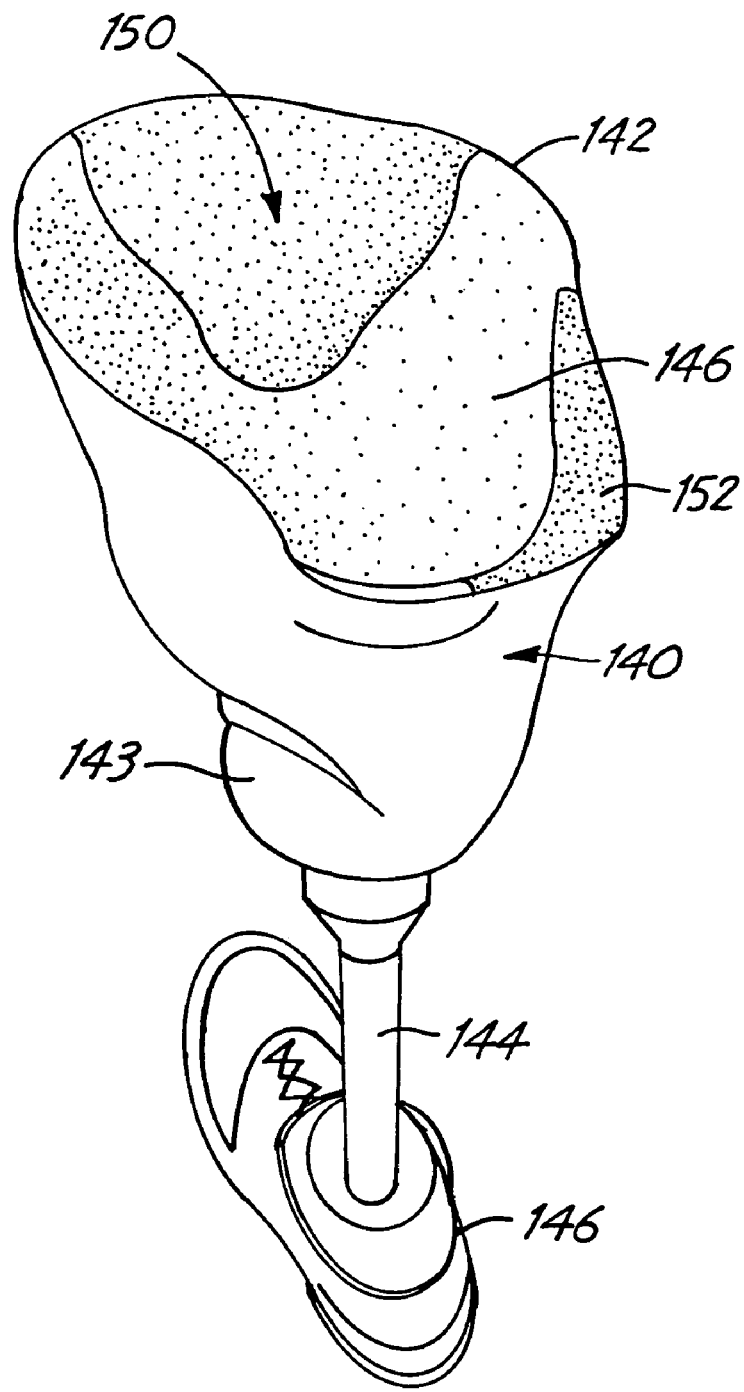

FIG. 5 is a cross sectional view of a modified aspect of the present invention;

FIG. 6 is a plan view of a further modified patch made according to the present invention;

FIG. 7 is a sectional view taken on line 7-7 in FIG. 6;

FIG. 8 is a plan view of a further modified patch made according to the present invention;

FIG. 9 is a sectional view of the patch shown in FIG. 8 taken on line 9-9 in FIG. 8;

FIG. 10 is a schematic representation of a typical shoe showing regions having patches made according to the present invention installed for reducing shear damage to tissue;

FIG. 11 is a perspective view of an ankle and foot orthosis showing locations where patches having a low friction surface according to the present invention are installed, and which can be installed either on the orthosis as shown, or as shown in FIG. 12 on a foot on which the orthosis will be worn;

FIG. 12 is a schematic showing of a foot and ankle indicating desired locations of low friction patches for an orthosis;

FIG. 13 is a top plan view of a prosthetic socket for a lower leg prosthesis showing regions on the interior of the socket where low friction pads would be installed to reduce tissue trauma caused by shear;

FIG. 14 is a schematic representation of a leg and knee that would fit into the prosthesis of FIG. 13, and showing locations of low friction patches made according to the present invention;

FIG. 15 is a perspective view of a longer leg prosthetic device having a socket for receiving the upper portion of a leg to which the prosthesis would be attached and illustrates locations of low friction patches made according to the present invention.

DETAILED DESCRIPTION OF THE PREFERRED EMBODIMENTS

Figure 1:
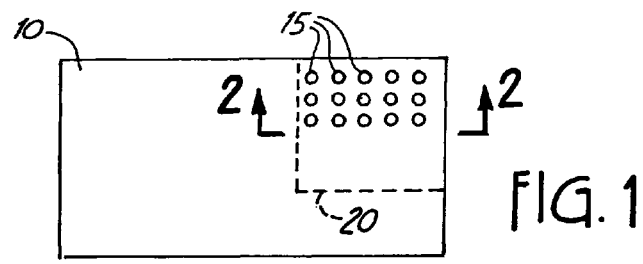
FIG. 1 is a plan view of a layer of material made with a low friction surface material according to the present invention.
Figure 2:
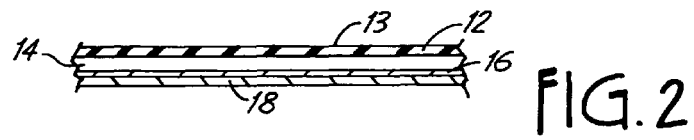
FIG. 2 is a sectional view taken on line 2-2 in FIG. 1 showing the layers used.

FIGS. 1 and 2 illustrate a simple form of the invention which includes a composite sheet 10 made in a suitable size, which can be used for cutting individual interface patches or pieces from the sheet. The composite sheet 10 includes a thin film or layer 12 of polytetrafluoroethylene (PTFE). Layer 12 is preferably bonded to a stretch fabric layer 14, such as Lycra or stretch nylon, which also is relatively thin. The top layer of PTFE can be in the range of 2.5 mils thick, and the layer of fabric 14 could be slightly thicker than that, as needed to make a suitable stretch weave. The PTFE film 12 is conformable and will stretch, so that the stretch fabric will cause the PTFE layer to move with it, if it is stretched in any direction. A thin layer of adhesive 16 is shown in the drawings on an opposite side or surface of fabric layer 14 from the PTFE layer 12. A suitable release paper 18 is provided over the adhesive on the fabric.

The sheet 10 can be used for cutting out various configuration, such as those shown in dotted lines at 20, for custom fitting patches of the low friction material 12. It can be seen that the low friction material film 12 has an upper surface 13 which faces, and supports the skin. Also as shown schematically perforations 15 can be provided for breathability of the patch. When the patch such as that shown by dotted lines 20 is placed on the skin, for an interface with a shoe, prosthesis, or orthosis, as desired the surface 13 faces away from the skin. The purpose of applying the patch is to lower the magnitude of tangential traction that the surface of loan object worn by a person can exert against the skin. The PTFE film is bonded to one surface of the fabric layer, and is available from Chemfab Corporation of Merrimack, N.H., USA.

Figure 3:
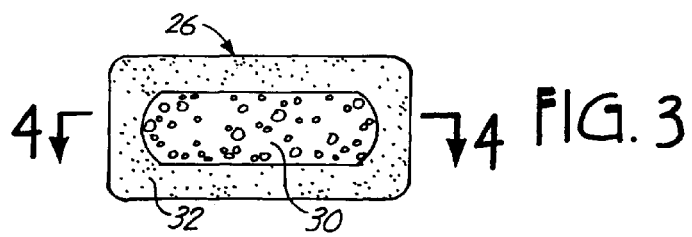
FIG. 3 is a plan view of a form of patch.
Figure 4:
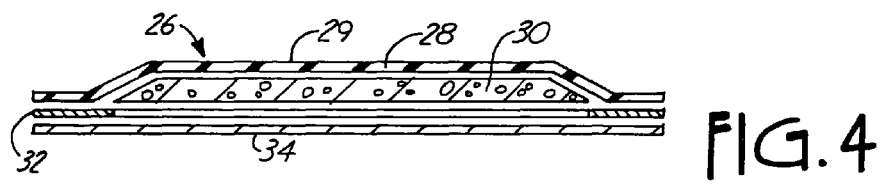
FIG. 4 is a sectional view of a patch made according to an aspect of the present invention, taken on line 4-4 in FIG. 3 including a layer of low friction material that will lower friction loads on the skin in a selected area.

The sheet 10 is usable in large areas, or can be cut for small areas as desired. Premanufactured special size and shape patches or pieces can be made, as shown in FIG. 3 where a patch 26 is illustrated in generally a rectangular configuration. An exploded section of the patch 26 is shown in FIG. 4, except that in FIG. 3 the release paper is shown removed to provide a view of a foam layer 30 around which the adhesive layer 32 extends. The sectional views are shown exploded, for illustration but the layers are bonded together in use.

The patch 26 comprises a film or layer 28 of the low friction material, such as PTFE, bonded to a plastic foam layer 30 that is of smaller size than the PTFE film layer. The foam 30 is shown in FIG. 4 to be substantially thicker than the PTFE film layer, but it can be any thickness desired. The pressure sensitive adhesive layer 32 is then applied, and can be provided only on the peripheral edges as shown in FIG. 3, to provide an open center where the foam layer 30 would be exposed for contact with the skin. A release paper layer 34 overlies the bottom of the patch. The exterior surface 29 of the PTFE film layer 28 provides the low friction surface for reducing shear and tangential traction against a support surface or material. The foam layer 30 may be in contact with the skin or the surface of the support to provide cushioning and protection. The foam layer 30 could be, for example, in the range of a quarter inch thick, but would have tapered or skived edges as shown so that the PTFE film layer 28 would conform well to the foam. The adhesive used is selected to bond to the PTFE layer so there is an adhesive edge for adhering the patch on the skin or other surface. The adhesive is a pressure sensitive adhesive.

The preformed patch 26 shown in FIG. 3 can be sized to be 2, 3, or 4 inches long, for example, with widths of 1, ½ and 2 inches. The patch 26 thus can be used for any application where a spot or region of skin is subject to shear and abrasion, so the tissue is becoming tender, to relieve the tangential traction on that portion of the skin.

FIG. 5 illustrates an exploded cross section of a modified patch 36 having the periphery shown in FIG. 3. The patch 36 has a PTFE film layer 38. The PTFE film layer 38 is bonded to a stretch fabric layer 40 such as stretch nylon or Lycra. A foam layer 42 is bonded to the fabric layer 40 in the center portions of the patch. The pressure sensitive adhesive layer 44 is placed on the surface of the fabric layer opposite from the low friction outer surface 39 of PTFE film layer 38. The adhesive layer 44 again can be formed as shown in FIG. 3 with a rim of adhesive surrounding an open center where the foam layer 42 is exposed. A release paper 46 is also provided on the patch as shown in cross section. As stated, the PTFE films can be perforated as desired.

The use of the stretch fabric 40 provides an additional layer of cushioning and protection, which can be stretched along with the PTFE film to fit rounded surfaces or irregularities. The foam layer 42 has its edges beveled, and the stretch fabric layer 40 and the PTFE film layer 38 will fit closely around the foam. The stretch fabric layer 40 is bonded to the PTFE film layer 38 before placing the foam in position, so both the fabric and the PTFE would be stretched at the same time. This bonding, again, is done commercially by Chemfab Corporation of Merrimack, N.H., USA. The PTFE film also can be bonded to leather and other fabrics by ChemFab Corporation.

Peripheral dimensions of the patches for the construction shown in FIG. 5 can be the same as those shown in connection with FIG. 3, and the bottom view would be the same as well. Of course other configurations such as elliptical shapes and the like can be used. The pressure sensitive adhesive layer 44 can extend all the way across the foam, so there is no open center, if desired.

In FIGS. 6 and 7 a modified form of the invention is shown, which has low coefficient of friction film on both surfaces of the patch, so when the patch that is shown in FIG. 7 is placed on a corn or callus, the surface in contact with the skin has the low coefficient of friction and the outwardly facing surface does also. The patch 50, as shown is elliptically shaped, and in FIG. 7 a cross sectional exploded view is illustrated. A PTFE film layer having a low coefficient of friction outer surface 53 is bonded to a stretch fabric layer 54 and then a foam layer 56 that has a hole 57 through the center is provided in the center portions of the patch 50. In this form of the invention, a layer 60 of PTFE film that is relatively small in size is positioned in the hole 57 in the foam and is bonded to the fabric layer for example with pressure sensitive adhesive. A pressure sensitive adhesive layer 58 is then bonded to the stretch fabric layer 54 and the underside of the foam layer 56 but surrounding the hole 57. A release paper layer 59 overlies the bottom surface of patch 50 and over the adhesive. The layer of PTFE film 60 is shown in both FIGS. 6 and 7, and has an outwardly facing low coefficient of friction surface 61 that will reduce any abrasion of skin that it contacts.

The foam layer 56 has a generally elliptically shaped periphery as shown in dotted lines in FIG. 6, and the overall configuration then would be a patch 50 that could be adhered to skin, to provide a low friction material directly against the skin with the small layer of film 60, and a larger area of low friction film defined by layer 52 that could engage the lining of a shoe or the inner surface of a sock or the like.

FIGS. 8 and 9 illustrate a further modified form of the invention comprising an elliptically shaped piece or patch 66 that is made of a layer 68 of PTFE film having an outer low coefficient of friction surface 69. Layer 68 is bonded to a stretch fabric layer 70. A second layer of PTFE film 72, is smaller in size than the top PTFE film layer 68 and the stretch fabric 70 and is bonded to the stretch fabric 70 in the center portions of the patch on an opposite side of the fabric from the PTFE film layer 68. This can be seen in FIG. 8.

A layer of pressure sensitive adhesive 74 is then applied to the peripheral rim area surrounding the film layer 72, and will provide for an adhesive layer of sufficient size to permit adhering the patch 70 to the skin, or objects or supports for the skin. A release paper layer 75 is provided. This patch is made without any cushioning or foam layer. The smaller center layer 72 of PTFE film does not have any adhesive between it and the skin, so this is not adhered to the skin, but has a low friction surface 73 that is free to slide against the skin. This reduces the friction on the load carrying surfaces significantly, and reduces trauma from shear, even when it is of low magnitude. Low magnitude shear can cause tissue damage if it cycles repeatedly.

FIG. 10 illustrates schematically a foot within a shoe drawn in phantom to illustrate in cross section, regions where high load and/or rubbing areas can benefit from the application of the low friction patches made according to the present invention. In FIG. 10, the bones of the foot are illustrated at 80, and they are shown within the outline of a shoe 82. High load bearing areas of course are located under the metatarsal heads 84, the heel or calcaneus 90, and the end of the toes, in particular the big toe 97. The metatarsal heads 84 are supported on a patch 86. This patch 86 can be on top of the insole 87 and thus between the sock (and foot) and the support provided by shoe 82. The patch 86 can be installed in the shoe 82 permanently, by sewing if desired. Patch 86 provides a low friction surface area where the sock can slide easily relative to the surface of the patch 86 and will not tend to abrade against the skin of the foot in the high load support area.

The patch or pad 86 can extend across the width of the metatarsals, so that the entire metatarsal head region (the metatarsal-phalangeal joint region) of the foot is supported on a relatively low friction surface. The patch or pad 86 preferably has an outer PTFE film layer, backed by a stretch fabric and held in place on the shoe insole. A foam layer as shown in FIG. 5 can be provided in the patch or pad 86, if desired.

Another region that can be supported is at the toe end surfaces, in particular the big toe, such as that shown with a pad 88 under end of the big toe 97. This is a region that is not subjected to extremely high loads, but there is a lot of cyclic loading, including shearing, as one moves. The toe supports forces as the person pushes off on each stride, particularly when running.

The heel bone or calcaneus indicated at 90 has a bony prominence 92, that is supported on a patch 94 having a low coefficient of friction outer surface region. The patch or pad 94 will provide support and reduce any shear loads if there is slippage during the stride. Additionally, the cushioning patches that are shown, having a foam layer can provide some cushioning support and conformability around protrusions in the heel bone to reduce trauma and damage.

A non-load-bearing area where cyclic shear loads can cause damage is shown above a toe where a joint may be deformed or contracted so the bone is raised up as shown at 96 and will tend to rub against an upper surface of the toe box 98 of the shoe 82. The installation of a pad 100 directly on the toe, or on the interior of the shoe on the top interior surface of the toe box will reduce the shear loading to a point where even cyclical loading will not cause shear damage, blistering, callusing or the like. In a nonweight-bearing area, therefore, the low friction surface patches also provide relief. Bonding PTFE film to leather permits lining the toe box of a shoe to reduce friction in the entire toe region.

The patches or pads of the present invention find needed application in ankle-foot orthoses. One such orthosis is shown in FIG. 11, at 104 and includes a foot support shell 106, and ankle and leg support shell 108 joined together with flexure members 110 in a conventional manner so that the foot shell 106 can be flexed relative to the leg support. The shells are open in the front and top, as can be seen, and a retaining strap 112 is used for retaining the leg in position. Additional securing devices can be used for the foot.

The interior surfaces of the shells 106 and 108 support the foot, the ankle, and the lower leg snugly, but there can be some sliding or shear forces generated. A patch 114 that is relatively large and which can be cut from the form of the invention shown in FIG. 1, is positioned in the longitudinal arch area. Suitable foams can be used between the shell surface and the pad, a low friction material PTFE is provided on the top surface of the patch that engages the underside of a foot in the orthosis, through a sock, in this high load support area. The pad or patch 114 can be configured to provide support in the arch area as well as reducing the friction loads that occur from any sliding, particularly under high forces. The patch 114 can be made as shown before with foam underneath the PTFE film layer. Use of a stretch fabric layer backing the PTFE film is desired because of some irregular contours that have to be followed on the formed foot shell 106.

The low friction surface pads used where there is flexing, insures that the shear loads are very low, and have the advantage of having foam attached or bonded to the film surface. Conventional foam pads are very high friction and will tend to cause tissue damage from repeated shear loads even though direct weight support is not present. Additionally, a medial leg support patch or pad shown at 120 can be provided above the ankle bone, and this includes foam padding behind a PTFE film layer for increasing or modifying the pressure distribution and provide increased corrective forces. The pad 120 can be again cut to the desired shape, and suitable foams can be used under the PTFE layer. Here, too, the pad preferably has the bonded stretch fabric beneath the outer PTFE film layer because of the need of conforming to irregular contours.

The edges of the shell can be lined with the low friction surface patches or pads 122 to reduce shear in these regions. The patches or pads can be folded over the edges and adhered in place. The main portion of the pads on the edges should be on the interior surfaces.

FIG. 12 illustrates a typical foot and lower ankle joint, and the region shown at 114A, where the pad or patch 114 would bear on the arch. The upper pad or patch region on the leg is shown at 120A.

FIG. 13 is a top view of a typical transtibial prosthetic leg 123. The prosthetic leg 123 includes a rigid socket 124 and a soft socket liner 125 which will receive a residual limb, and support the residual leg at and just below the knee. In such a prosthesis, there are regions where tissue is thin over bony prominences, such as at the lateral, anterior and bony prominences near the top of the tibia and the tibia crest. These regions are also shown in FIG. 13, and pads shown at 126 and 128 for bony prominences are placed appropriately in the socket liner 125. The socket has a rigid shell 124 that normally has a liner 125 made of a suitable material such as a foam or gel. The patches according to the present invention provide for low friction support between a covering sock or layer of material and the supporting surface. In FIG. 14, the tibial crests, the medial and lateral bony prominences near the top of the tibia are indicated at 130A, 126A, and 128A. The patches or pads can have foam underneath the low friction film layer. The low friction surfaces reduce shear loading against the skin and subcutaneous tissue when the skeleton moves relative to the socket. The outer shell 124 supports a lower leg portion of the prosthesis.

Additionally, the tibial crest pad 130 of FIG. 13 is aligned with the tibial crest shown at 130A in FIG. 14. The pad 130 has the PTFE film outer layer bonded to a stretch fabric because of irregular contours that have to be followed on the socket. Suitable foam padding can be provided to insure some load distribution and conformability onto the tibial crest.

Another bony area of support for a lower leg prosthesis is the fibular head shown at 132A in FIG. 14. A fibular head pad 132 (FIG. 13) is placed to cushion the lateral side of the remaining limb and around the rear of the leg. The head of the fibula bone is quite close to the skin surface in these locations, so that very high pressure and shear loads are carried in this region and damage can easily occur. The patches of the present invention reduce the friction between the limb and the supporting surfaces of the socket, to provide for a smooth surface that is very low friction so that the tissue is not subjected to shear loading. The upper edges of the socket 124 can be lined with patches, if desired.

FIG. 15 is a view of a socket used for a full leg prosthesis (trans-femoral amputation), where support is provided at the femur and pelvic bones. The shell shown at 140 has an upper socket region 142, and the lower portion 143 that supports a knee joint, pylon 144 and a foot prosthesis 146.

In this instance, a large patch or pad 150 made according to the present invention can be provided in the frontal area where loads will be directly applied to relatively soft tissue, and this will reduce frictional loads as soft tissue tends to move, for example, the residual limb tends to move in and out as the upper leg flexes between sitting and standing positions. the reduction in frictional loads is achieved by having the PTFE film layer on the exterior and the patch or pad adhered to the socket so that it does not slide on the socket. Friction loads on the remaining limb portion is greatly reduced.

Also the patch or pad 152 avoids shear as weight is applied to the socket, which causes relative shifting of the limb and shell.

Additionally, an irregularly shaped patch or pad 152 is provided along a rear rim or edge portion of the socket, where relatively high loads are encountered. This pad or patch 152 can be provided with the stretch fabric layer bonded to PTFE film for conformability. A foam layer can underlie the stretch fabric. The layer of PTFE on the exterior reduces friction in the high load contact area between the socket support regions and the remaining limb and pelvic bones. Other regions can also be covered with the pads of the present invention to provide a low friction interface between the remaining limb and the socket. Foam layers can be used where needed.

A series of tests were conducted between the available products on the market for corn pads, liners, and the like, used in shoes and other regions where support relative to the skin is desired, as well as other materials, such as adhesive bandages. The following Tables 1, 2 and 3 show average coefficient of friction values and standard deviations for dry and wet interface tests. Nine trials were performed for each test in measuring coefficient of friction, and the results averaged.

In the tests a sled surface was covered with the test material and moved across the sock material while the force measurements were made.

TABLE 1

| | DRY TEST | | WET TEST | |
|---|---|---|---|---|
| | Ave | St Dev | Ave | St Dev |
| SURFACE MATERIAL SOFT MATERIALS | | | | |
| BockLite 1/8" | 0.49 | 0.10 | 0.56 | 0.03 |
| Orthopedic Cowhide | 0.49 | 0.11 | 0.68 | 0.03 |
| PPT with Ultrilure ® Top Coverup | 0.57 | 0.07 | 0.57 | 0.02 |
| IPOCON ® Gel with Lycra Top Coverup | 0.41 | 0.08 | 0.48 | 0.02 |
| Moleskin J&J | 0.63 | 0.03 | 0.87 | 0.03 |
| PE Lite 1/16" | 0.51 | 0.08 | 0.48 | 0.02 |
| Plastazote .125" | .57 | 0.06 | 0.51 | 0.05 |
| Diab-A-Sheet - PPT side up, plastazote down | 0.55 | 0.09 | 0.67 | 0.03 |
| Russett Cow Leather | 0.41 | 0.15 | 0.62 | 0.06 |
| PRESENT INVENTION | | | | |
| Pad of FIG. 4 | 0.16 | 0.03 | 0.16 | 0.02 |
| Pad of FIG. 2 | 0.16 | 0.01 | 0.17 | 0.01 |

TABLE 2

| | DRY TEST | | WET TEST | |
|---|---|---|---|---|
| | Ave | St Dev | Ave | St Dev |
| SURFACE MATERIAL BANDAGES | | | | |
| Band-Aid ® Clear From J & J | 0.47 | 0.01 | 0.53 | 0.01 |
| Band-Aid ® Large From J & J | 0.46 | 0.04 | 0.53 | 0.03 |
| Band-Aid ® Plastic From J & J | 0.45 | 0.02 | 0.51 | 0.03 |

TABLE 2-continued

|  | DRY TEST | | WET TEST | |
|---|---|---|---|---|
|  | Ave | St Dev | Ave | St Dev |
| Blister-Care From Curad ® | 0.78 | 0.01 | 0.76 | 0.07 |
| Clean Seals From 3M | 0.64 | 0.02 | 0.57 | 0.02 |
| Duoderm CGF From Convatec | 0.38 | 0.03 | 0.30 | 0.01 |
| Nexcare Active Strips ™ From 3M | 1.01 | 0.02 | 0.61 | 0.01 |
| Sheer Bandages From Walgreens | 0.59 | 0.04 | 0.58 | 0.04 |
| PRESENT INVENTION | | | | |
| Pad of FIG. 4 | 0.16 | 0.03 | 0.16 | 0.02 |
| Pad of FIG. 2 | 0.16 | 0.01 | 0.17 | 0.01 |

TABLE 3

|  | DRY TEST | | WET TEST | |
|---|---|---|---|---|
|  | Ave | St Dev | Ave | St Dev |
| SURFACE MATERIAL PLASTICS | | | | |
| Orthoplast | 0.29 | 0.02 | 0.46 | 0.09 |
| Modified Polyethylene | 0.28 | 0.03 | 0.30 | 0.03 |
| CO Polyester | 0.27 | 0.04 | 0.41 | 0.01 |
| Polypropylene | 0.23 | 0.02 | 0.34 | 0.05 |
| PRESENT INVENTION | | | | |
| Pad of FIG. 4 | 0.16 | 0.03 | 0.16 | 0.02 |
| Pad of FIG. 2 | 0.16 | 0.01 | 0.17 | 0.01 |

In Table 1 above, Bocklite is a product manufactured by Otto Bock Othopedic, Inc. Of Minneapolis, Minn.; Orthopedic Cowhide and Russett Cowhide leather are available from Roden Leather of Royal Oaks Mich.; Diab-A-Sheet, a composite sheet of Plastazote and PPT foam layers and PPT with Ultrilure® top cover are both available from The Langer Biomechanics Group Inc of Deer Park, N.Y.; IPOCON® gel with Lycra top cover is sold by IPOS Orthopedics Industry, Niagara Falls N.Y.; Moleskin is an adhesive bandage sold by J.N. Johnson Sales of Minneapolis, Minn.; PE Lite and Plastazote (a polyethylene film) are sold by Pel Supply Company of Cleveland, Ohio.

In Table 2, all Band-Aid® products and Orthoplast are made by Johnson & Johnson Consumer Product, Inc. of Skillman, N.J.; Clean Seals and Nexcare™ Active Strips™ are from 3M Health Care of St. Paul, Minn.; Blister-Care is distributed by A Beiersdorf Co. of Milford, Ohio; Duoderm CGF is distributed by the ConvaTec Division of E.R. Squibb & Sons, Inc. of Montreal, Quebec, Canada; Sheer bandages are from Walgreens Co. of Deerfield, Ill.

In Table 3, modified Polyethylene and Co-Polyester are distributed by American Plastics of Ft. Worth, Tex.; and the Polypropylene is from Seelye Plastics, Inc. of Bloomington, Minn.

It can be seen that the pads of the present invention maintain lower friction characteristics whether the cotton socks used were wet or dry. For testing the "wet" socks were saturated with steam at 150° F. Some of the material such as BockLite did not vary substantially between wet and dry conditions (high friction in both cases), but other commonly used natural liners such as orthopedic cowhide, moleskin, russett leather, and the like increased in coefficient of friction substantially in the presence of moisture. The presence of moisture is common where perspiration will cause socks to become damp.

Studies in relation to the causation of ulcers on the skin indicate that when there is a relatively high level of shear, the pressure necessary to produce blood flow occlusion is reduced substantially from when little shear is present. This means that providing low friction surface patches in critical areas, where shear forces can be generated will tend to reduce the likelihood of formations of ulcers or calluses.

In bony areas, such as the lower leg area, shear displacements from pistoning motions result in higher shear strains where the tissue is thinnest, the shear strain is a function of the tissue thickness to the bony support. Thus, at the front edge of the leg, a similar shear displacement of the outer skin results in a higher shear strain than at the rear or fleshy part of the leg. Shear strain is a function of the shear displacement divided by the thickness of tissue between the surface of the skin and the bony support.

Thus, the present invention relates to the use of a very low friction film under both dry and moist conditions, having a support surface that substantially reduces the coefficient of friction that is active to cause shear loads on skin supported on that particular film, whether through a sock, a cloth material of some kind, or directly against the skin. In so doing, the likelihood of ulceration, calluses, or similar problems caused by shear strains and stresses is reduced. The size and shape of the pads can be custom made as desired, the pads can be used with or without foam cushioning. The pressure sensitive adhesive used is a convenient way of applying pads in regions where temporary relief may be made, but the film can be also permanently stitched into the interfaces of a shoe or boot, or of a prosthetic device, such as a prosthetic limb. Installation of pads in orthoses is also very convenient. Treatment can be carried out for spots that seem to be developing sores or which become tender, by placing a low friction patch between the load bearing area of the body or skin and the object that is applying the load so that shear is reduced in that localized area. Thus, the method of treatment includes adding suitable sized patches in regions between tender or sole areas of the skin and the shoe or support object.

Although the present invention has been described with reference to preferred embodiments, workers skilled in the art will recognize that changes may be made in form and detail without departing from the spirit and scope of the invention.

What is claimed is:

1. A method of reducing trauma to highly shear loaded tissue supported under load against exposed support surfaces of an object only in selected region of the exposed support surface, including selecting at least one region of high load where shear load on tissue is likely to cause or has caused discomfort, and providing a plurality of low friction surface patches comprising a polytetrafluoroethylene film having a bonded stretch fabric on one side of the film such that the film moves with the stretch fabric and releasably securable to the exposed support surface, applying at least one of the patches between at least one selected region of high load and the exposed support surface of the object and conforming the stretch fabric to contours of the support surface in the at least one selected region by supporting the tissue such that only the selected region is supported on a low friction surface patch.

* * * * *